United States Patent
Durand et al.

(10) Patent No.: US 8,938,103 B2
(45) Date of Patent: Jan. 20, 2015

(54) APPARATUS AND METHOD FOR DETECTING AND MEASURING BIOMOLECULAR INTERACTIONS

(75) Inventors: Nicolas Durand, Blonay (CH); Iwan Märki, Yverdon (CH); Theo Lasser, Denges (CH)

(73) Assignee: Ecole Polytechnique Ferderale de Lausanne (EPFL), Lausanne (CH)

(*) Notice: Subject to any disclaimer, the term of this patent is extended or adjusted under 35 U.S.C. 154(b) by 176 days.

(21) Appl. No.: 13/581,761

(22) PCT Filed: Feb. 25, 2011

(86) PCT No.: PCT/IB2011/050808
§ 371 (c)(1),
(2), (4) Date: Sep. 27, 2012

(87) PCT Pub. No.: WO2011/107916
PCT Pub. Date: Sep. 9, 2011

(65) Prior Publication Data
US 2013/0016887 A1      Jan. 17, 2013

(30) Foreign Application Priority Data

Mar. 1, 2010    (WO) .................. PCT/IB2010/050867

(51) Int. Cl.
  *G06K 9/00*     (2006.01)
  *G01N 21/64*    (2006.01)
  *C12N 15/82*    (2006.01)
  *G01N 35/00*    (2006.01)
(52) U.S. Cl.
  CPC ........ *G01N 21/6452* (2013.01); *G01N 21/6428* (2013.01); *G01N 2035/00158* (2013.01)

USPC .......................................... 382/128; 435/468

(58) Field of Classification Search
  USPC ......... 382/128, 129, 130, 131, 132, 133, 134; 977/772, 958; 250/214.1, 251
  See application file for complete search history.

(56) References Cited

U.S. PATENT DOCUMENTS

| 7,531,786 B2 * | 5/2009 | Cunningham et al. ..... 250/214.1 |
| 7,777,476 B2 * | 8/2010 | Hu et al. ..................... 324/71.4 |
| 2006/0028955 A1 | 2/2006 | Wakita et al. |

FOREIGN PATENT DOCUMENTS

| WO | WO 02/10448 | 2/2002 |
| WO | WO 2007/041340 | 4/2007 |

OTHER PUBLICATIONS

International Search Report for PCT/IB2011/050808, mailed Jul. 15, 2011.
Written Opinion of the International Searching Authority for PCT/IB2011/050808, mailed Jul. 15, 2011.

* cited by examiner

*Primary Examiner* — Abolfazl Tabatabai
(74) *Attorney, Agent, or Firm* — Nixon & Vanderhye P.C.

(57) ABSTRACT

A method and system for the rapid detection of biomolecular interactions, the system comprising a sensing platform which comprises a primary support structure including recesses designed to be located in front of a detection unit, said recesses containing one or several arrays of biosensors, said system furthermore comprising a reader unit for optical excitation and detection.

11 Claims, 3 Drawing Sheets

ND MEASURING
BIOMOLECULAR INTERACTIONS

APPARATUS AND METHOD FOR DETECTING AND MEASURING BIOMOLECULAR INTERACTIONS

This application is the U.S. national phase of International Application No. PCT/IB2011/050808, filed 25 Feb. 2011, which designated the U.S. and claims priority to WO International Application No. PCT/IB2010/050867, filed 1 Mar. 2010, the entire contents of each of which are hereby incorporated by reference.

FIELD OF INVENTION

The invention relates to the detection and the measurement of biomolecular interactions, in particular when several samples have to be quickly handled.

BACKGROUND OF THE INVENTION

Biosensors are defined as fluidic systems with cavities and/or channels, which are used to measure the molecular interactions of diffusing biomolecules with other at the surfaces of the biosensors immobilized molecules. A majority of the current biosensor developments are intended for bioengineering and biotechnology applications. In the scope of this invention, biosensors are used to measure biomolecular interactions for in vitro diagnostic applications.

Swiss patent application CH 01824/09 discloses biosensors for the detection of biomolecular interactions. The biosensors were described for a use with a confocal microscope. However, confocal microscope reading is difficult to automate, leading to long measurement times.

Current technologies for the detection of biomolecular interactions can be divided in two categories: (a) the labeled techniques and (b) the label-free techniques.

Among the labeled techniques, the widely used methods are fluorescence, colorimetry, radioactivity, phosphorescence, bioluminescence and chemiluminescence. Functionalized particles such as nanoparticles or magnetic beads can also be considered as labeling techniques. Their advantages are the sensitivity in comparison to label-free methods and the molecular specificity due to specific labeling.

Fluorescence microscopy allows to measure the presence and the concentration of biomolecules specifically labeled with a fluorescent molecule called a fluophore. The specimen is illuminated with light of a specific wavelength, which brings it to an excited state, leading to an emission of light at a longer wavelength. The emission is measured by a detector, which allows quantifying the number of fluophores in the measurement volume.

Fluorescence correlation spectroscopy (FCS), as a known representative of single molecule detection techniques, allows to access, across the fluctuation analysis of fluorescently labeled single biomolecules, static and dynamic molecular parameters, such as the mean number of molecules, their diffusion behavior and kinetic binding constants. This single molecule detection tool enables to measure the specificity of the biomolecule interaction, without being influenced by the presence of the fluorescent molecules outside the detection volume.

In close relation to FCS several other techniques, known as Photon Counting Histogram (PCH), Fluorescence Intensitiy Distribution Analysis (FIDA) or Fluorescence Lifetime spectroscopy (FLS), use the intrinsic fluorophore mediated properties of single biomolecules for measuring the chemical binding constants, concentration or number of molecules, diffusion properties, etc. All these techniques are substantially compatible with the disclosed invention.

Nanoparticle-based microscopy is an emerging technique allowing detecting the presence of functionalized nanoparticles that can be attached on biomolecules of interest. This technique has several advantages over fluophores such as chemical stability and no photobleaching.

Among the label-free techniques, the widely used are electrochemical biosensors, referring to amperometric, capacitive, conductometric or impedimetric sensors, which have the advantage of being rapid and inexpensive. They measure the change in electrical properties of electrode structures as biomolecules become entrapped or immobilized onto or near the electrode. However, all these concepts lack molecular specific contrast, sensitivity and reliability.

Surface plasmon resonance (SPR) is also a label-free optical technique for monitoring biomolecular interactions occurring in very close vicinity of a transducer gold surface, and has lead to great potential for real-time studying surface-confined affinity interactions without rinsing out unreacted or excess reactants in sample solutions. However, this method is limited to ensemble measurements, meaning that it is not single-molecule sensitive.

The other important technologies for biomolecular diagnostics are Western and Northern blots, protein electrophoresis and polymerase chain reaction (PCR). However, these methods require highly concentrated analytes.

OBJECTIVES

It is an object of this invention to overcome the limitations of the biosensors use described in Swiss patent application CH 1824/09 by providing a simple handling platform to rapid and automated sensing of multiple different biomolecular interactions.

Another object of the invention is to use modified compact disc readers to perform the measurement of fluorescence inside the biosensors.

Another object of the invention is to use modified compact disc readers to precisely control the position of the reading unit by means of rotation and translation in order to scan every biosensors disposed on the platform.

Still another object of the invention is to use modified compact disc readers to precisely control the position of the reading lens in order to focus the laser beam inside the measurement area of the biosensors disposed on the platform.

These and other objects of the present invention will be better understood with the following drawings and preferred embodiments.

SUMMARY OF THE INVENTION

This invention is based on the combination of nanofluidic biosensors, a biocompatible sensing platform containing recesses and a reader unit.

This invention is based on the assembly of the nanofluidic biosensors within recesses of the biocompatible sensing platform.

Finally, this invention highlights the possibility to modify the detection apparatus of standard compact disc readers in order to perform integrated microscopy for rapid and automated analysis with the above mentioned sensing platform.

BRIEF DESCRIPTION OF THE DRAWINGS

FIG. 1 shows a cross section of the biomolecular diagnostics system composed of a primary structure 110, containing one or several cavities 111 or capsules, and on which is attached a thin transparent film 120 on the bottom. An array of biosensors 130 may be disposed onto the thin transparent film inside the cavities 111, or may be inserted inside openings 121.

Figure 1A:
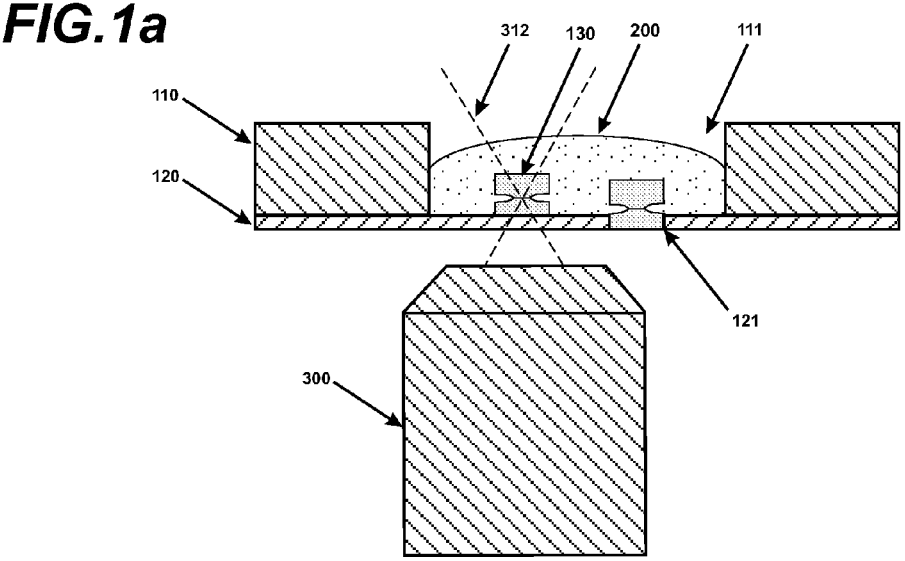
FIG. 1A shows that a solution containing fluorescent biomolecules to analyze 200 may be deposited inside one or several of the cavities 111 or of the capsules 114 in a way that the biosensors 130 are completely immersed.

For the fluorescence measurements, the excitation beam 312 produced by the excitation laser 311 is collimated by the lens 316, cleaned up by the excitation filter 317, and directed by two dichroic mirrors 318 and 319, the mirror 313, and the lens 314 to be focused inside the biosensor 130. Inside the biosensor 130 fluorescent biomolecules are excited and emit the fluorescent signal 321, which is directed by the lens 314, the mirror 313, the dichroic mirror 319, the emission filter 320 and the lens 322 onto the detector 315. The detector 315 can either be a detector surface or an optical fiber guiding the fluorescent signal to a fibered detector.

DETAILED DESCRIPTION OF THE INVENTION

As used herein, the term "biomolecules" is intended to be a generic term, which includes for example (but not limited to) polyclonal antibodies, monoclonal antibodies, Fab fragments, recombinant antibodies, globular proteins, amino acids, nucleic acids, enzymes, lipid molecules and polysaccharides.

As used herein, the term "sensing platform" is intended to be a generic term, which means a device containing one or several arrays of biosensors. It is designed in order to facilitate the reception of the liquid solution to analyze. As used herein, the term "cavities" is intended to be a generic term, which means well-defined wells in the sensing platform, inside which are disposed the biosensors array and that will contain the liquid solution during the measurement. As used herein, the term "capsules" is intended to be a generic term, which means well-defined container disposed in the sensing platform, inside which are disposed the biosensors array and that will contain the liquid solution during the measurement.

As used herein, the term "compact disc reader" is intended to be a generic term, which means standard reader of compact disc (CD), digital versatile disc (DVD), Laserdisc, Blu-ray or other optical media technologies.

As used herein, the term "reading unit" is intended to be a generic term, which means the device containing the measurement system, including the compact disc reader.

The present invention aims to provide a simple method for detecting biomolecular interactions by combining microfluidic and nanofluidic biosensors described in the patent [1], a biocompatible sensing platform containing cavities or capsules, and a reader unit.

Figure 1B:
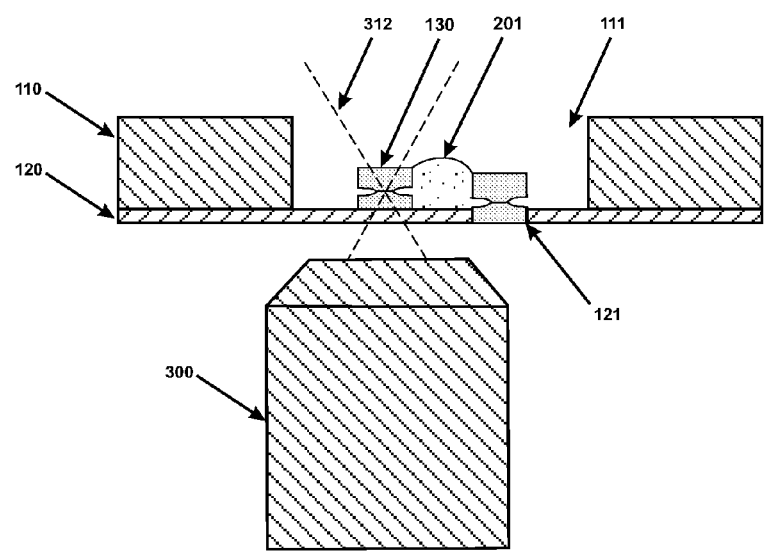
FIG. 1B illustrates that a solution containing the fluorescent biomolecules to analyze 200 may be deposited in a way that only a part of the biosensors 130 are immersed. A reading unit 300, is approached to the thin film 120, or to the opening 121, in order to perform the measurement with a laser beam 312 directly inside one or several of the biosensors 130, from the backside.

As shown in FIG. 1, the sensing platform is composed of a primary support structure 110 containing cavities 111 or openings 113. This primary structure may be a single component or may be composed of a primary structure, on which is attached a transparent biocompatible thin film 120. An array of biosensors 130 may be disposed in the capsules 114 or on the thin film 120 within the cavities of the primary structure 110. The solution 200 containing the fluorescent biomolecules to detect is deposited directly in one of the cavities 111 or capsules 114 in order to fill the biosensors 130 by capillarity, The solution 200 can also be disposed in a way that only a part of the biosensor 130 is immersed. A reading unit 300 is approached by the opposite side of the thin film 120. Its laser beam 312 is focused inside the biosensors 130, such as the measurement volume is always right-positioned in the detection area during every measurement.

The biomolecules contained in the solution 200 diffuse in every biosensor, interact with those preliminary fixed on the biosensors surfaces, and may create a molecular complex (depending on the specificity). The immobilized biomolecules and those freely diffusing across the optical detection volume are both detected by the reading unit 300 that is inserted or connected to a computer or an analyzing unit. Finally, the measurements are directly presented to the user who will interpret their meaning.

Figure 2:
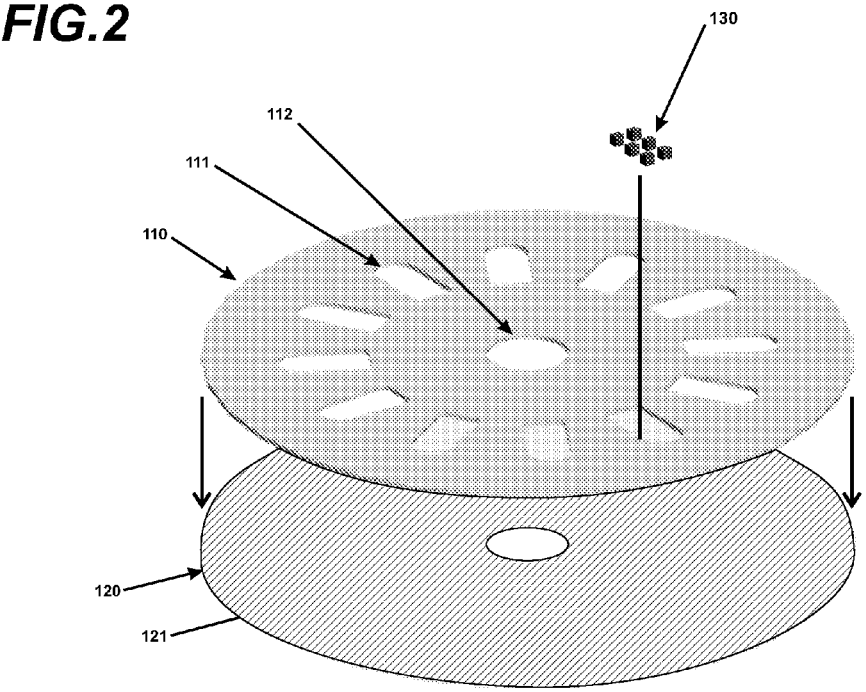
FIG. 2 represents a perspective view of a primary structure 110, containing several sensing cavities 111 and a central cavity 112 used by the reading unit 300 for the positioning control of the sensing platform 100. The thin transparent film 120, also containing a central aperture 121 used for the positioning control, is added on the bottom of the primary structure 110. Biosensor arrays 130 are assembled inside the cavities 111 directly on the thin transparent film 120.

A possible principle of assembly of the sensing platform 100 is illustrated in FIG. 2. First, the primary support structure 110 containing the cavities 111 and a central aperture 112 is used to place the assembly in the measurement position. The transparent biocompatible thin film 120, also containing a central aperture 121 that is larger than the one of the primary structure 110, is added. Biosensor arrays 130 are assembled on the thin film 120 within the cavities 111 of the primary structure 110.

Figure 3:
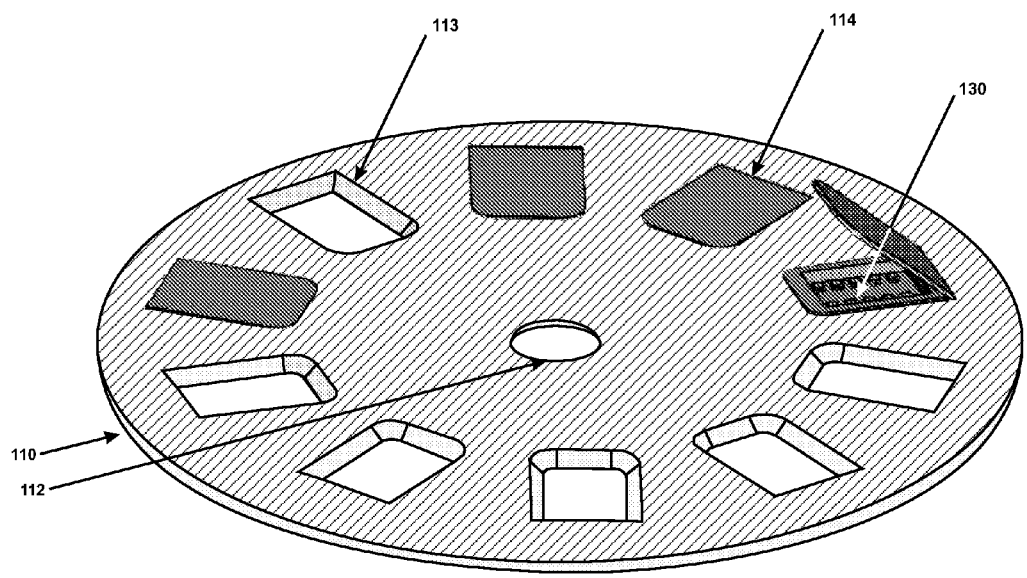
FIG. 3 represents a perspective view of a primary structure 110, containing several openings 113 and a central cavity 112 used by the reading unit 300 for the positioning control of the sensing platform 100. Several capsules 114 are disposed in the openings 113 and may be opened before or after insertion. Arrays of biosensors 130 are present in each capsule 114.

Another possible principle of assembly of the sensing platform 100 is illustrated in FIG. 3. First, the primary support structure 110 containing the openings 113 and a central aperture 112 is used to place the assembly in the measurement position. Capsules 114, which contain biosensors array 130, are disposed in the openings 113.

Figure 4:
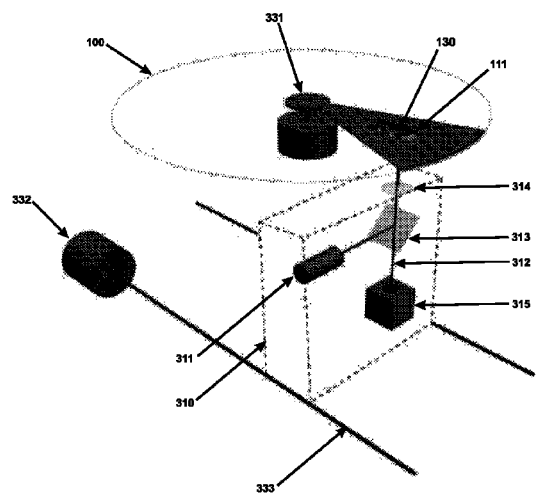
FIG. 4 is a 3D illustration of the sensing concept. The sensing platform 100 is actuated by the motor 331 in order to place the capsules or the sensing cavities 111 containing the biosensors 130 in the sensing position. The linear motor 332 controls the transversal position of the integrated measurement unit 310, which is disposed on a rail system 333, in order to position the measurement volume in the biosensor of interest. The excitation beam 312 is produced by the excitation laser 311 and is deflected on the dichroic minor 313 before to pass through the lens 314. When focalized in the right position inside one of the biosensors 130, the excitation beam 312 excites fluorescently labeled biomolecules of the solution 200, which emit photons that are collected by the lens and finally detected by the detector 315.

The sensing principle is presented in FIG. 4. The sensing platform 100 is positioned by the motor 331 in order to place sensing cavity 111 and especially one of the biosensors 130 in the sensing position. The linear motor 332 controls the transversal position of the integrated measurement unit 310, which is disposed on a rail system 333, in order to position precisely the measurement volume inside the biosensor of interest. The excitation beam 312 is produced by the laser 311 and is deflected on the dichroic mirror 313 before passing through the lens 314. When focused in the right height position inside the biosensor, the laser beam 312 excites fluorescently labeled biomolecules, which emit photons that are collected by the lens 314 and finally detected by the detector 315. The detector 315 is controlled by an electronic interface, which is connected to a computer or an analyzing unit that will present the measurements to the user.

Figure 5:
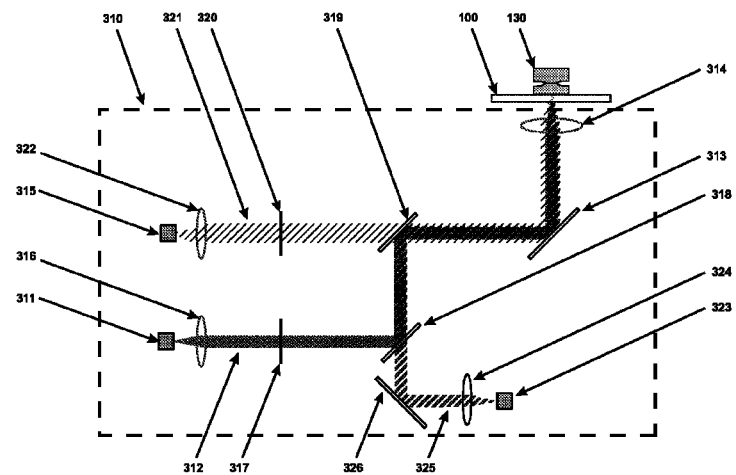
FIG. 5 represents an illustration of the optical system 310 containing the light source 323 for the positioning of the sensing platform 100 and the biosensor 130. The positioning beam is directed by the lens 324, the minor 326, the dichroic minors 318 and 319, the mirror 313 and the lens 314 onto the sensing platform where the positioning beam is partly reflected and directed back by the lens 314, the minor 313, the dichroic mirror 319, the emission filter 320 and the lens 322 onto the detector 315.

The optical system 310 is presented in FIG. 5. By means of the light source 323 the biosensors 130 on the sensing platform 100 is correctly positioned for the fluorescence measurement. The positioning beam 325 is collimated by the collimating lens 324, deflected by the minor 326, transmitted through the dichroic mirror 318, partly deflected by the dichroic minor 319, deflected by the mirror 313 and then focused onto the sensing platform 100 by the lens 314. Part of the positioning beam 325 is reflected by the sensing platform 100 and the biosensor 130, collected by the lens 314, deflected by the mirror 313, partly transmitted through the dichroic mirror 319 and the emission filter 320, and focused by the lens 322 onto the detector 315. The signal from the positioning beam 325 is then analyzed for the correct positioning of the biosensors 130 in preparation of the fluorescent measurement.

The excitation beam 312 is produced by the excitation laser 311 and collimated by the collimating lens 316, cleaned up by the excitation filter 317, deflected by two dichroic minors 318 and 319, and the minor 313, in order to be focused on the sensing platform 100 and inside the biosensor 130 by the lens 314. Inside the biosensor 130 fluorescent biomolecules are excited, which then emit the fluorescent signal 321 being collected by the lens 314, deflected by the minor 313, transmitted through the dichroic minor 319 and the emission filter 320, and focused by the lens 322 onto the detector 315. The detector 315 can either be a detector surface or an optical fiber guiding the fluorescent signal to a fibered detector.

The method of measurement presented in this invention shows great promise for the detection, enumeration, identification and characterization of biomolecular interactions. Applications of the present invention can cover biomedical, biological and food analysis as well as fundamental studies in analytical and bioanalytical chemistry.

The invention claimed is:

1. A system for detecting and measuring biomolecular interactions including a sensing platform which comprises a primary support structure including recesses designed to be located in front of a measurement unit, said recesses containing one or several arrays of microfluidic and nanofluidic biosensors with lateral-apertures, said system furthermore comprising a reader unit for optical excitation and detection, and wherein said recesses each have an area from 1 $mm^2$ to 1 $m^2$.

2. A system according to claim 1 wherein each of said recesses is defined by a lateral wall formed by said support structure and a bottom either also formed by said support structure or by a transparent biocompatible thin film.

3. Sensing platform according to claim 2, wherein said transparent biocompatible film has a thickness from 10 nm to 3 mm.

4. A system according to claim 1 wherein each of said recesses is a capsule.

5. System according to claim 1 wherein the shape of said sensing platform is a flat disc or polygon, having an area from 10 $mm^2$ to 1 $m^2$, and a height from 100 nm to 2 cm; said sensing platform also has a central cavity for controlling the position of the platform.

6. Sensing platform according to claim 1 wherein said array of biosensors composed from 1 to 10,000 individual biosensors that may be coated with different biomarkers.

7. Sensing platform according to claim 1 containing of compact disc compatible reading and recording areas for information exchange.

8. Sensing platform according to claim 1 wherein said reading unit is an optical system comprising an excitation light source, a positioning light source and a detector that is a single-photon detector, a detector array (CMOS or CCD) or an avalanche photodiode (APD).

9. A method for detecting and measuring biomolecular interactions that comprises:
   a. a sensing platform, containing recesses inside which are disposed arrays of biosensors, as defined in claim 1;
   b. placing the sensing platform in a reading unit;
   c. filling said biosensor(s) by depositing onto said biosensor(s) an aqueous solution containing the biomolecules to analyze;
   d. using the reading unit, connected to a computer or an analyzing unit, by determining the presence and the diffusion kinetics of labeled biomolecules inside each biosensor.

10. Method according to claim 9 wherein said biomolecules are proteins, DNA, RNA, antibodies, amino acids, nucleic acids, enzymes, lipid molecules or polysaccharides.

11. Method according to claim 9 wherein said biomolecules are fluorescently-labeled or nanoparticle-labeled molecules.

* * * * *